(12) United States Patent
Portmann et al.

(10) Patent No.: US 6,740,669 B1
(45) Date of Patent: May 25, 2004

(54) CRYSTAL MODIFICATION OF 1-(2,6-DIFLUOROBENZYL)-1H-1,2,3-TRIAZOLE-4-CARBOXAMIDE AND ITS USE AS ANTIEPILEPTIC

(75) Inventors: Robert Portmann, Pratteln (CH); Urs Christoph Hofmeier, St. Pantaleon (CH); Andreas Burkhard, Basel (CH); Walter Scherrer, Rheinfelden (CH); Martin Szelagiewicz, Münchenstein (CH)

(73) Assignee: Novartis AG, Basel (CH)

( * ) Notice: Subject to any disclaimer, the term of this patent is extended or adjusted under 35 U.S.C. 154(b) by 801 days.

(21) Appl. No.: 09/125,329

(22) PCT Filed: Jun. 8, 1998

(86) PCT No.: PCT/EP98/03427

§ 371 (c)(1),
(2), (4) Date: Sep. 8, 1998

(87) PCT Pub. No.: WO98/56772

PCT Pub. Date: Dec. 17, 1998

(30) Foreign Application Priority Data

Jun. 10, 1997 (CH) .............................................. 1404/97

(51) Int. Cl.$^7$ ................... A61K 31/4192; C07D 249/04
(52) U.S. Cl. ...................................... 514/359; 548/255
(58) Field of Search .......................... 514/359; 548/255

(56) References Cited

U.S. PATENT DOCUMENTS 4,789,680 A * 12/1988 Meier .......................... 514/359

FOREIGN PATENT DOCUMENTS

EP         199 262 A     10/1986

OTHER PUBLICATIONS

Munzel I., Progress in Drug Research, 10 (1966) pp. 227–230 XP002078506 Basel, CH.*
Munzel II, Progress in Drug Research, 14 (1970) pp. 309–321, XP 0020785047 Basel, CH.*
Munzel K., Progress in Drug Research, vol. 10, pp. 227–330 (1966).
Munzel K., Progress in Drug Research, vol. 14, pp. 309–321 (1970).
Chemical & Engineering News, pp. 32–34 (2003).
U.S. Pharmacopia, pp. 1843 & 1844 (1995).
Concise Encyclopedia Chemistry, pp. 872 & 873 (1993).

* cited by examiner

*Primary Examiner*—Patricia L. Morris
(74) *Attorney, Agent, or Firm*—Joseph J. Borovian

(57) ABSTRACT

The invention relates to the novel modification A or A' of the compound 1-(2,6-difluorobenzyl)-1H-1,2,3-triazole-4-carboxamide of the formula

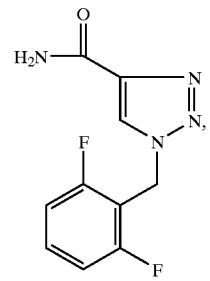

its use and pharmaceutical preparations comprising this crystal modification.

21 Claims, 2 Drawing Sheets

CRYSTAL MODIFICATION OF 1-(2,6-DIFLUOROBENZYL)-1H-1,2,3-TRIAZOLE-4-CARBOXAMIDE AND ITS USE AS ANTIEPILEPTIC

BACKGROUND OF THE INVENTION

The compound 1-(2,6-difluorobenzyl)-1H-1,2,3-triazole-4-carboxamide of the formula

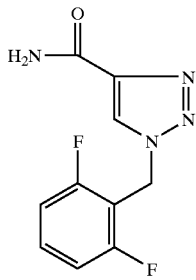

is described in the European Patent Application with the Publication No. 0 199 262 A2 (EP 199262), for example in Example 4. Valuable pharmacological properties are attributed to this compound; thus, it can be used, for example, as an antiepileptic. The compound 1-(2,6-difluorobenyl)-1H-1,2,3-triazole-4-carboxamide is obtained according to EP 199262, starting from 2,6-difluorobenzyl azide via the formation of 1-(2,6-difluorobenzyl)-1H-1,2,3-triazole-4-carboxylic acid, the procedure being analogous to Example 2.

EP 199262 provides no information at all about possible crystal modifications obtained. If the method according to the Example 4 is used in conjunction with Example 2, the crude 1-(2,6-difluorobenzyl)-1H-1,2,3-triazole-4-carboxamide product obtained is finally crystallized from ethanol. However, EP 199262 gives no indication that such recrystallization is specifically to be applied, or on particular conditions that might be adopted. It has now surprisingly been found that the different crystal modifications (polymorphism) characterized below can be prepared by choice of specialty selected process conditions, for example through the choice of an appropriate solvent for the recrystallization or the duration of the recrystallization.

DESCRIPTION OF THE INVENTION 1-(2,6-Difluorobenzyl)-1H-1,2,3-triazole-4-carboxamide can be obtained in the novel crystal modifications A, A', B and C. These crystal modifications differ with respect to their thermodynamic stability, in their physical parameters, such as the absorption pattern of IR and Raman spectra, in X-ray structure investigations and in their preparation processes.

The invention relates to the novel crystal modifications A and A' preparation and use in pharmaceutical preparations comprising the crystal modifications.

The modification A', compared with A, has defects in the crystal lattice. These are detectable, for example, by X-ray analysis, e.g. by smaller line spacings with otherwise predominantly identical lines or bands.

The novel crystal modification A of 1-(2,6-difluorobenzyl)-1H-1,2,3-triazole-4-carboxamide melts at 242° C. (239–245° C.).

In the FT infrared (FT-IR) spectrum (KBr pellet—transmission method), modification A or A' differs from modifications B and C predominantly in the shape and in the relative intensity of many bands. Particularly characteristic are the bands at 3412 cm$^{-1}$ and 3092 cm$^{-1}$ [cf. FIG. 1], which are not present in the Fr-IR spectra of the modifications B and C. In the range 4000–600 cm$^{-1}$, inter alia the following bands are obtained for modification A: 3412, 3189, 3092, 1634, 1560, 1473, 1397, 1325, 1300, 1284, 1235, 1125, 1053, 1036, 1014, 885, 840, 799, 781, 723, 688 and 640 cm$^{-1}$. For example, the apparatus IFS 88 (Bruker) can be used for the recording of each of the FT-IR spectra.

In the FT Raman spectrum (powder—reflection method 180°), the modification A or A' differs from modifications B and C predominantly in the shape and in the relative intensity of many bands. Particularly characteristic are the band at 1080 cm$^{-1}$ [cf. FIG. 2], which is not present in the Raman spectra of the modifications B and C. In the range 3400–300 cm$^{-1}$, inter alia the following bands are obtained for the modification A: 3093, 2972, 1628, 1614, 1558, 1465, 1446, 1393, 1279, 1245, 1147, 1080, 1061, 1036, 1014, 840, 724, 691, 667, 550, 499, 437 and 368 cm$^{-1}$. For example, the apparatus RFS 100 (Bruker) can be used for the recording of each of the FT Raman spectra.

The novel modification A has an X-ray powder pattern with characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, 2.81 Å [cf. Table 1]. The measurement can be carried out, for example, in transmission geometry on an FR 552 Guinier camera from Enraf-Nonius, Deft (The Netherlands), using copper K$\alpha_1$ radiation (wavelength λ=1.54060 Å). The patterns recorded on X-ray film were measured using an LS-18 line scanner from Johannsson, Täby (Sweden) and evaluated using the Scanpi software (P. E. Werner, University of Stockholm).

Characteristic for the novel modification A is the thermogram in differential scanning calorimetry. It has an endothermic peak in the range from 230° C. to 260° C. The peak temperature is 239–245° C., and the endothermic signal is 209 J/g+/−10 J/g. The measurement was carried out on a Perkin Elmer DSC 7 in a closed pan with a heating rate of 20 K/minute. The typical sample quantity is about 4 mg. As a typical distinguishing feature compared with the modifications B and C, the thermogram of the modification A has no further thermal signal.

Crystals of the modfication A' have the same crystal structure as modification A. They differ from the modification A in the X-ray powder pattern in that they have slightly smaller line spacings between specific pairs of lines. These are the pairs of lines with the following interplanar spacings: 3.68 Å and 3.64 Å, 3.51 Å and 3.48 Å, 3.19 Å and 3.15 Å.

In the FT-IR spectrum (KBr pellet—transmission method), the modification B differs from the modification A or A' and C predominantly in the shape and in the relative intensity of many bands. Particularly characteristic is a band at 1678 cm$^{-1}$ [cf. FIG. 1], which is not to be observed in the corresponding spectra of the modifications A and C. In the range 4000–600 cm$^{-1}$, inter alia the following bands are obtained for the modification B: 3404, 3199, 3125, 1678, 1635, 1560, 1475, 1393, 1357, 1322, 1286, 1237, 1051, 1036, 1028, 889, 837, 800, 719, 667 and 645 cm$^{-1}$. For example, the apparatus IFS 85 (Bruker) can be used for recording of each of the FT-IR spectra.

In the FT Raman spectrum (powder—reflection method 180°), the modification B differs from the modifications A or A' and C predominantly in the shape and in the relative intensity of many bands. Particularly characteristic are the bands at 3166 cm$^{-1}$ and 1086 cm$^{-1}$ [cf. FIG. 2], which are not present in the Raman spectra of the modifications A and C. In the range 3400–300 cm$^{-1}$, inter alia the following bands are obtained for the modification B: 3166, 3089, 2970, 1678, 1628, 1614, 1559, 1464, 1441, 1391, 1275, 1244, 1147, 1086, 1062, 1036, 1014, 839, 773, 724, 690, 668, 595, 549, 500, 493, 430 and 365 cm$^{-1}$. For example, the apparatus RFS 100 (Bruker) can be used for recording of each of the Fr Raman spectra.

The modification B has an X-ray powder pattern with characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å, 2.83 Å [cf. Table 1].

In the thermogram in differential scanning calorimetry, the modification B has, in addition to an endothermic signal in the range from 230° C. to 260° C. (peak temperature 239–245° C.), a weak thermal signal at 205° C. (180–220° C.) as a typical distinguishing feature compared with the modifications A or A' and C.

In the FT-IR spectrum (KBr pellet—transmission method), the modification C differs from the modifications A or A' and B predominantly in the shape and in the relative intensity of many bands. Particularly characteristic is a band at 3137 cm$^{-1}$ [cf. FIG. 11], which is not to be observed in the corresponding spectra of the modifications A and B.

In the range 4000–600 cm$^{-1}$, inter alia the following bands are obtained for the modification C: 3396, 3287, 3137, 1657, 1631, 1602, 1559, 1475, 1392, 1323, 1287, 1237, 1122, 1104, 1047, 1035, 1012, 876, 839, 797, 773, 729 and 653 cm$^{-1}$. For example, the apparatus IFS 85 (Bruker) can be used for recording of each of the FT-IR spectra.

In the FT Raman spectrum (powder—reflection method 180°), the modification C differs from the modifications A or A' and B predominantly in the shape and in the relative intensity of many bands. Particularly characteristic are the bands at 3137 cm$^{-1}$ and 1602 cm$^{-1}$ [cf. FIG. 2], which are not present in the Raman spectra of the modifications A and B. In the range 3400–300 cm$^{-1}$, inter alia the following bands are obtained for the modification C: 3137, 3080, 3012, 2971, 1673, 1629, 1602, 1561, 1436, 1271, 1248, 1105, 1065, 1035, 1013, 839, 800, 767, 726, 690, 672, 593, 549, 500, 492, 435 and 370 cm$^{-1}$. For example, the apparatus RFS 100 (Bruker) can be used for recording of each of the FT Raman spectra.

The modification C has an X-ray powder pattern with characteristic lines with interplanar spacings (d values) of 9.0 Å, 4.73 Å, 4.65 Å, 3.75 Å, 3.54 Å, 3.42 Å, 325 Å [cf. Table 1]. In the thermogram in differential scanning calorimetry, the modification C has, in addition to an endothermic signal in the range of 230° C. to 260° C. (peak temperature 239–245° C.), a very broad, weak, exothermic signal in the region of 180° C. compared with the modifications A or A' and B.

TABLE 1

Characterization of the modifications A, B and C (X-ray powder patterns):

| Modification A: | | Modification B: | | Modification C: | |
|---|---|---|---|---|---|
| d [Å] | Intensity | d [Å] | Intensity | d [Å] | Intensity |
| 10.9 | weak | 11.0 | medium | 9.0 | medium |
| 10.5 | medium | 8.3 | medium | 7.0 | weak |
| 6.6 | weak | 8.1 | very weak | 5.49 | weak |
| 5.63 | weak | 5.68 | very weak | 5.11 | very weak |
| 5.25 | weak | 5.18 | very strong | 4.80 | weak |
| 5.14 | medium | 5.11 | weak | 4.73 | strong |
| 4.94 | weak | 4.88 | medium | 4.65 | very strong |
| 4.84 | very strong | 4.80 | strong | 4.47 | very weak |
| 4.55 | strong | 4.71 | very weak | 4.19 | very weak |
| 4.42 | very weak | 4.61 | weak | 4.11 | very weak |
| 4.34 | medium | 4.45 | weak | 3.98 | very weak |
| 4.23 | very weak | 4.42 | strong | 3.83 | very weak |
| 4.16 | weak | 4.33 | very strong | 3.75 | strong |
| 4.07 | medium | 4.19 | medium | 3.73 | weak |
| 4.01 | weak | 4.12 | strong | 3.54 | medium |
| 3.68 | very weak | 4.09 | weak | 3.50 | weak |
| 3.64 | very weak | 3.99 | very weak | 3.42 | strong |
| 3.60 | weak | 3.95 | very weak | 3.25 | medium |
| 3.56 | weak | 3.84 | weak | 2.88 | very weak |
| 3.51 | medium | 3.81 | medium | 2.80 | very weak |
| 3.48 | medium | 3.65 | weak | 2.74 | very weak |
| 3.38 | very weak | 3.61 | very weak | 2.67 | very weak |
| 3.25 | strong | 3.58 | very weak | 2.64 | weak |
| 3.19 | medium | 3.54 | weak | | |
| 3.15 | medium | 3.50 | medium | | |
| 3.11 | weak | 3.47 | very weak | | |
| 3.07 | medium | 3.41 | medium | | |
| 2.93 | very weak | 3.36 | very strong | | |
| 2.87 | very weak | 3.32 | strong | | |
| 2.81 | medium | 3.28 | medium | | |
| 2.76 | weak | 3.24 | medium | | |
| 2.73 | very weak | 3.10 | weak | | |
| 2.68 | weak | 3.07 | weak | | |
| 2.62 | very weak | 3.05 | medium | | |
| 2.53 | weak | 2.93 | weak | | |
| 2.43 | weak | 2.88 | weak | | |
| 2.40 | very weak | 2.87 | very weak | | |
| | | 2.83 | medium | | |
| | | 2.66 | weak | | |
| | | 2.63 | very weak | | |
| | | 2.55 | weak | | |
| | | 2.50 | weak | | |
| | | 2.46 | weak | | |
| | | 2.44 | weak | | |
| | | 2.37 | weak | | |
| | | 2.35 | weak | | |

Single Crystal X-ray Analysis

Crystal quality and unit cell of modifications A, B, and C were verified by Weissenberg and precession photographs. The intensities were measured on a four-axis Nonius CAD-4 diffractometer. The structures were solved with the SHELXS-97 and refined with the SHELXL-97 software.

Modification A

Space group: Pna2$_1$—orthorhombic

Cell dimensions:

| a = 24.756 (5)Å | b = 23.069 (4)Å | c = 5.386 (1)Å |
|---|---|---|
| v = 3075.9 Å$^3$ | Z = 12 | D$_x$ = 1.543 gcm$^{-3}$ |
| v per formula: | V$_z$ = 256.3 Å$^3$ | |

9011 unique reflections; 2479 thereof significant with I>2σ (I). 557 parameters refined. Position of all H atoms found by difference Fourier maps and refined isotropically. Reliability index R$_1$: 3.65% (wR$_2$ for all 9011 reflections: 11.34%).

Modification B

Space group: P⁻1—triclinic
Cell dimensions:

| a = 5.326(1) Å | b = 11.976(2) Å | c = 17.355(3) Å |
|---|---|---|
| α = 107.22(3)° | β = 92.17(3)° | γ = 102.11(3)° |
| v = 1027.9 Å³ | Z = 4 | $D_x$ = 1.539 gcm⁻³ |
| v per formula | $V_z$ = 257.0 Å³ | |

4934 unique reflections; 834 thereof significant with I>2σ (I). 232 parameters refined. Position of all H atoms found by difference Fourier maps and refined isotropically. Reliability index $R_1$: 4.20% ($wR_2$ for all 4934 reflections: 7.93%).

Modification C

Space group: P2₁/C—monoclinic
Cell dimensions:

| a = 10.982(2) Å | b = 5.350(1) Å | c = 17.945(3) Å |
|---|---|---|
| | β = 91.59(1)° | |
| v = 1053.9 Å³ | Z = 4 | $D_x$ = 1.501 gcm⁻³ |
| v per formula: | $V_z$ = 263.5 Å³ | |

3073 unique reflections; 1071 thereof significant with I>2σ (I). 187 parameters refined. Position of all H atoms found by difference Fourier maps and refined isotropically. Reliability index $R_1$: 5,02% ($wR_2$ for all 3073 reflections: 14.55%). Modifications A, A', B and C have valuable pharmacological properties; in particular, they can be used for the treatment of epilepsy.

The modification A or A' has significant advantages compared with the modification B and compared with the modification C. Thus, for example, comprehensive thermodynamic investigations such as thermomicroscopy, X-ray powder diffractometry, DSC, solubility tests and other experiments, have shown that the modification A or A' surprisingly has substantially better thermodynamic stability than the modifications B and C. Modification C, which can be obtained only under specific conditions, is the least stable of the three modifications. The crystals of the modification C are converted into modification B at as low as room temperature within a few weeks. The modification C is converted either into the modification A or A' or into the modification B, depending on experimental conditions.

It is particularly important for a drug that its pharmaceutical formulation ensures high and reproducible stability over a long period. These preconditions are fulfilled by incorporation of the compound 1-(2,6-difluorobenzyl)-1H-1,2,3-triazole-4-carboxamide of the crystal modification A or A', owing to its high thermodynamic stability. In particular, this is displayed in a solid pharmaceutical dosage form.

A constant stability also permits reproducible bioavailability of an active ingredient. If an active ingredient is subjected to a conversion process, this may readily also cause the bioavailability to fluctuate, which is undesirable. Accordingly, pharmaceutical active ingredients or polymorphic forms thereof which are of primary interest for pharmaceutical developments are those which exhibit high stability and do not have the above-mentioned disadvantages. The crystal modification A or A' fulfills these preconditions.

Furthermore, the modification A or A' has, for example, a slower dissolution rate in water or in gastric fluid (so-called "slow-release effect"). This effect can be utilized primarily for long-term therapy where a slow or delayed release is desired.

The invention relates to the modification A of 1-(2,6-difluorobenzyl)-1H-1,2,3-triazole-4-carboxamide, characterized by the following absorptions in the infrared spectrum (KBr pellet—transmission method): bands at 3092 cm⁻¹ and 3412 cm⁻¹.

The invention relates to the modification A of 1-(2,6-difluorobenzyl)-1H-1,2,3-triazole-4-carboxamide, characterized by characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.07 Å and 2.81 Å, determined by means of an X-ray powder pattern.

The invention relates to the modification A of 1-(2,6-difluorobenzyl)-1H-1,2,3-triazole-4-carboxamide, characterized by the characteristic lines with interplanar spacings (d values) as shown in Table 1.

The invention relates to the modification A of 1-(2,6-difluorobenzyl)-1H-1,2,3-triazole-4-carboxamide, characterized by an endothermic peak in the range from 230° C. to 260° C., the peak temperature being 239–245° C. and the endothermic signal being 209 J/g+/−10 J/g.

Furthermore, the invention relates to the crystal modification A' which, compared with modification A, has defects in the crystal lattice.

The invention relates to the modification A' which, compared with modification A, has smaller line spacings between the pairs of lines with interplanar spacings 3.68 Å and 3.64 Å, 3.51 Å and 3.48 Å and 3.19 Å and 3.15 Å.

The invention relates to the essentially pure form of the modification A or A' of 1-(2,6-difluorobenzyl)-1H-1,2,3-triazole-4-carboxamide. The term "essentially pure form" means purity of >95%, in particular >98%, primarily >99%, based on the modification A or A'.

The invention relates to pharmaceutical preparations comprising the modification A or A' of 1-(2,6-difluorobenzyl)-1H-1,2,3-triazole-4-carboxamide. The invention relates in particular to corresponding pharmaceutical preparations for the treatment of epilepsy and subindications thereof. The invention relates to the use of the modification A or A' of 1-(2,6-difluorobenzyl)-1H-1,2,3-triazole-4-carboxamide for the preparation of pharmaceutical preparations, in particular for the treatment of epilepsy and subindications thereof.

The novel modification A or A' of 1-(2,6-difluorobenzyl)-1H-1,2,3-triazole-4-carboxamide can be used, for example, in the form of pharmaceutical preparations which comprise a therapeutically effective amount of the active ingredient, if desired together with inorganic or organic, solid or liquid, pharmaceutically usable carriers, which are suitable for enteral, for example oral, or parenteral administration. Furthermore, the novel modification A or A' of 1-(2,6-difluorobenzyl)-1H-1,2,3-triazole-4-carboxamide can be used in the form of preparations which can be administered parenterally or of infusion solutions. The pharmaceutical preparations may be sterilized and/or may comprise excipients, for example preservatives, stabilizers, wetting agents and/or emulsifiers, solubilizers, salts for regulating the osmotic pressure and/or buffers. The present pharmaceutical preparations comprise from about 0.1% to 100%, in particular from about 1% to about 50%, of lyophilisates to about 100% of the active ingredient.

The invention also relates to the use of modification A or A' of 1-(2,6-difluorobeanzyl)-1H-1,2,3-triazole-4- carboxamide as a drug, preferably in the form of pharmaceutical preparations. The dosage may depend on various factors, such as method of administration, species, age and/or individual condition. The doses to be administered daily are between about 0.25 and about 10 mg/kg in the case of oral administration, and preferably between about 20 mg and about 500 mg for warm-blooded species having a body weight of about 70 kg.

The preparation of modification A or A' is carried out, for example, as described in the embodiments below.

Preparation of 1-(2,6-difluorobenzyl)-1H-1,2,3-triazole-4-carboxamide

EXAMPLE 1

A suspension of methyl 1-(2,6-difluorobenzyl)-1H-1,2,3-triazole-4-carboxylate (about 62 parts by weight), methanol (475.2 parts by weight) and anhydrous ammonia (29.4 parts by weight) is stirred for about 24 hours at 50–55° C. in a closed vessel. The suspension is cooled to about 20° C. and stirred for about a further 2 hours. The product is isolated by filtration, washed with methanol (240 parts by weight) and dried at 40–60° C. in vacuo. Yield: 57.2 parts by weight= 98%. Modification A.

The starting compounds can be prepared, for example, as follows:

A mixture of 1-(2,6-difluorobenzyl)-1H-1,2,3-triazole-4-carboxylic acid (167.1 parts by weight), methanol (552 parts by weight) and 96% sulfuric acid (35.7 parts by weight) is stirred for about 5 hours at 60–66° C. The suspension is cooled to about 20° C. and stirred for about a further 2 hours. The product is isolated by filtration and washed with methanol (198 parts by weight). A yield of about 160 parts by weight is obtained by drying at 40–60° C. in vacuo.

EXAMPLE 2

1 N sodium hydroxide solution (0.11 ml) is added to a mixture of 4-cyano-1-(2,6-difluorobenzyl)-1H-1,2,3-triazole (2.20 g) and water (44 ml) at an external temperature of 95–100° C. while stirring. After 90 minutes, the suspension is cooled to 10° C. and the product is isolated by filtration, washed with water and dried at about 60° C. in vacuo. 1-(2,6-Difluorobenzyl)-1H-1,2,3-triazole-4-carboxamide is obtained in this manner, yield: 99.2% by weight, Modification A.

The starting material can be prepared, for example, as follows:

4-Cyano-1-(2,6-difluorobenzyl)-1H-1,2,3-triazole

A mixture of 2,6-difluorobenzyl azide (34.2 g), 2-chloroacrylonitrile (17.73 g) and water (125 ml) is stirred for 24 hours at about 80° C. By increasing the external temperature to about 130° C., excess 2-chloroacrylonitrile is distilled off. The semisolid mixture is cooled to about 40° C., cyclohexane (50 ml) is added to the suspension and the mixture is brought to about 20° C. and stirred for about 2 hours. The product is isolated by filtration and washed with cyclohexane (75 ml) and then with water (50 ml). The moist product is mixed with water (100 ml), the suspension is filtered and the product is washed with water (50 ml) and dried at about 60° C. in vacuo. Yield: 38.04 g=86%.

Examples of the Recrystallization of 1-(2,6-difluorobenzyl)-1H-1,2,3-triazole-4-carboxamide

EXAMPLE 3

1-(2,6-Difluorobenzyl)-1H-1,2,3-triazole-4-carboxamide (75.0 g) is dissolved in formic acid (360 ml) at 50–55° C. by stirring. The solution is discharged in the course of 1 hour onto stirred methanol (375 ml) at about 20° C., a suspension-forming. After stirring has been continued for 2 hours at about 20° C., the product is isolated by filtration, washed with methanol (750 ml) and dried at about 60° C. in vacuo. Yield: 69.6 g=92.8%. Modification A.

EXAMPLE 4

1-(2,6-Difluorobenzyl)-1H-1,2,3-triazole-4-carboxamide (22.86 kg) is dissolved in formic acid (111.6 kg) at 58–63° C. while stirring. The solution is discharged in the course of about 2 hours onto stirred methanol (131.9 l) at 20–25° C., after which washing with formic acid (7.6 kg) is carried out. A suspension forms. After stirring has been continued for at least 3 hours at about 20° C., the product is isolated by filtration and washed wit methanol (187.5 l). By drying in vacuo at about 60° C., the product is obtained as modification A in a yield of 93–94%.

EXAMPLE 5

1-(2,6-difluorobenzyl)-1H-1,2,3-triazole-4-carboxamide (pure active ingredient, 4.0 g) is dissolved in 96% ethanol (500 ml, without denaturing agent) at about 80° C. while stirring. The solution is filtered into a suction bottle (1 liter) at about 20° C. (glass suction filter, pore size 10–20 $\mu$m), A suspension forming. After stifing has been continued for 5 minutes at about 20° C. and for 15 minutes at about 0° C., the product is isolated by filtration (about 0° to about 20° C.). The solvent-moist product (9.6 g) is investigated without subsequent drying. Modification A'.

FORMULATION EXAMPLE 1

Film-coated tablets each containing, for example, 100, 200 or 400 mg of modification A or A' of 1-(2,6-difluorobenzyl)-1H-1,2,3-triazole-4-carboxamide with the following composition per dosage unit:

|  | mg | mg | mg |
|---|---|---|---|
| Core material |  |  |  |
| Active ingredient | 100.00 | 200.00 | 400.00 |
| Anhydrous, colloidal silica | 0.88 | 1.75 | 3.5 |
| Microcrystalline cellulose | 36.62 | 73.25 | 146.50 |
| Hydroxypropylmethyl-cellulose | 5.00 | 10.00 | 20.00 |
| Lactose | 20.00 | 40.00 | 80.00 |
| Magnesium stearate | 2.00 | 4.00 | 8.00 |
| Maize starch | 10.00 | 20.00 | 40.00 |
| Sodium carboxymethyl-cellulose | 5.00 | 10.00 | 20.00 |
| Sodium laurylsulfate | 0.50 | 1.00 | 2.00 |
| Film coat |  |  |  |
| Hydroxypropylmethyl-cellulose | 3.22 | 6.43 | 12.87 |
| Red iron oxide | 0.04 | 0.09 | 0.18 |
| Polyethylene glycol 8000, flakes | 0.58 | 1.16 | 2.32 |
| Talc | 2.33 | 4.66 | 9.31 |
| Titanium dioxide | 0.83 | 1.66 | 3.32 |

The active ingredient is granulated with demineralized water. Milled lactose, maize starch, Avicel PH 102, cellulose-HP-M-603 and sodium laurylsulfate are added to the above mixture and granulated with demineralized water.

The moist material is dried and milled. After the addition of the remaining ingredients, the homogeneous mixture is compressed to give tablet cores having the stated active ingredient content.

The tablet cores are coated with the film coat which is formed from the appropriate ingredients, the latter being dissolved or being suspended in water or in small amounts of ethanol with 5% of isopropanol.

Figure 1:
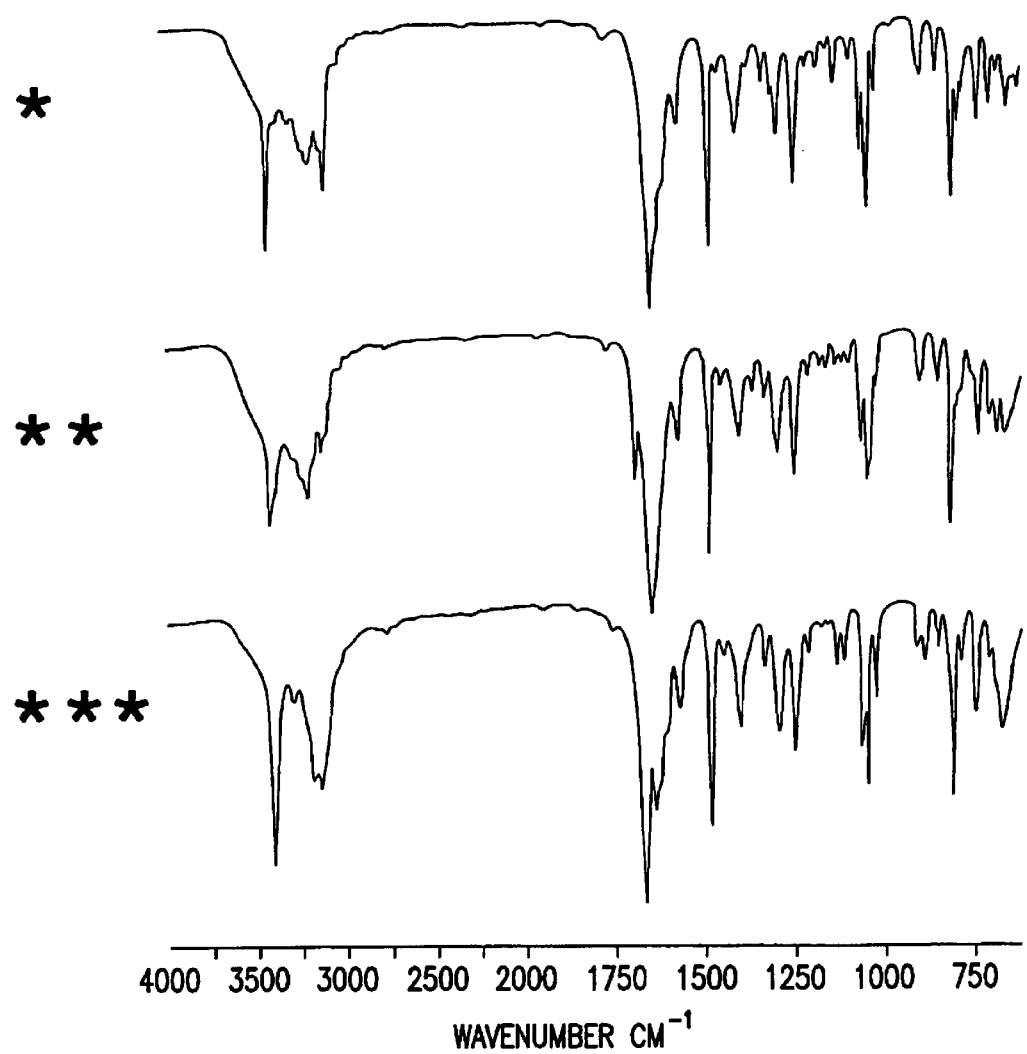
FIG. 1 shows the FT-IR spectra of the KBr pellets of modifications A, B and C.
Figure 2:
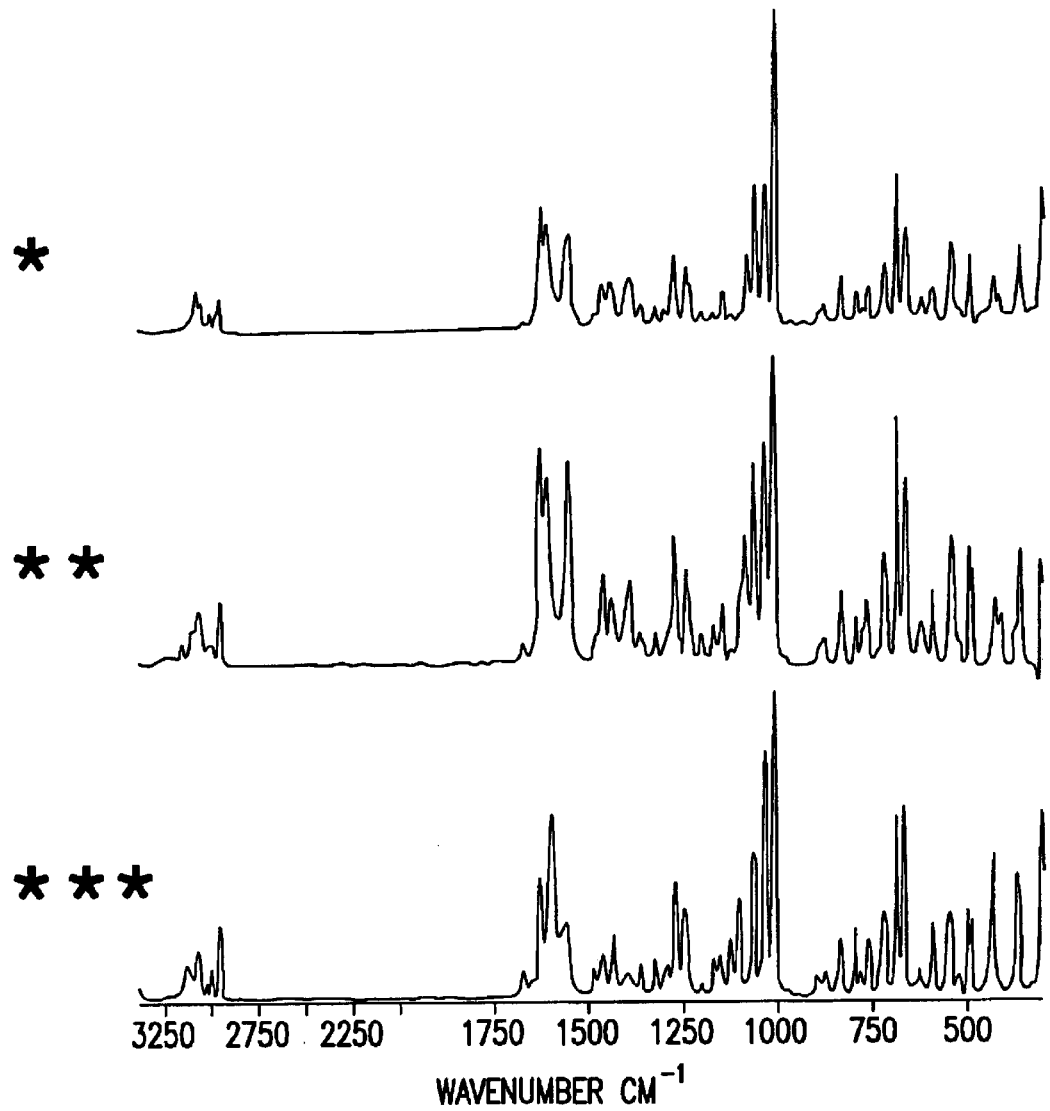
FIG. 2 shows the FT-Raman spectra-of the powder of modification A, B and C.

In both Figures, the modification a is denoted by the symbol*, the modification b by the symbol and the modification C by the symbol*.

What is claimed is:

1. Crystal modification A of the compound 1-(2,6-difluorobenzyl)-1H-1,2,3-triazole-4-carboxamide of the formula

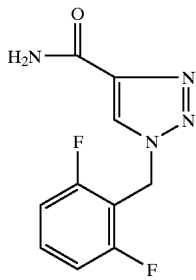

characterized by characteristic lines at interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, 2.81 Å, determined by means of an X-ray powder pattern.

2. The crystal modification according to claim 1, characterized by an X-ray powder pattern having the following characteristic lines at interplanar spacings (d values) of 10.9 Å (weak), 10.5 Å (medium), 6.6 Å (weak), 5.63 Å (weak), 5.25 Å (weak), 5.14 Å (medium), 4.94 Å (weak), 4.84 Å (very strong), 4.55 Å (strong), 4.42 Å (very weak), 4.34 Å (medium), 4.23 Å (very weak), 4.16 Å (weak), 4.07 Å (medium), 4.01 Å (weak), 3.68 Å (very weak), 3.64 Å (very weak), 3.60 Å (weak), 3.56 Å (weak), 3.51 Å (medium), 3.48 Å (medium), 3.38 Å (very weak), 3.25 Å (strong), 3.19 Å (medium), 3.15 Å (medium), 3.11 Å (weak), 3.07 Å (medium), 2.93 Å (very weak), 2.87 Å (very weak), 2.81 Å (medium), 2.76 Å (weak), 2.73 Å (very weak), 2.68 Å (weak), 2.62 Å (very weak), 2.53 Å (weak), 2.43 Å (weak), 2.40 Å (very weak).

3. The crystal modification according to claim 1, characterized by the following absorptions in the FT-IR spectrum (KBr pellet—transmission method) 3092 cm$^{-1}$ and 3412 cm$^{-1}$.

4. The crystal modification according to claim 3, characterized by the following absorptions in the FT-IR spectrum (KBr pellet—transmission method): 3412, 3189, 3092, 1634, 1560, 1473, 1397, 1325, 1300, 1284, 1235, 1125, 1053, 1036, 1014, 885, 840, 799, 781, 723, 688 and 640 cm$^{-1}$.

5. The crystal modification according to claim 1, characterized by the following absorptions in the FT-Raman spectrum (powder—reflection method 180°): 3093, 2972, 1628, 1614, 1558, 1465, 1446, 1393, 1279, 1245, 1147, 1080, 1061, 1036, 1014, 840, 724, 691, 667, 550, 499, 437 and 368 cm$^{-1}$.

6. The crystal modification A according to claim 1, characterized by an endothermic peak in the range from 230° C. to 260° C., the peak temperature being 239–245° C., and the endothermic signal being 209 J/g+/−10 J/g.

7. The crystal modification A' of the compound 1-(2,6-difluorobenzyl)-1H-1,2,3-triazole-4-carboxamide, characterized in that it is identical to the modification A according to claim 1 but has defects in the crystal lattice.

8. The crystal modification A' according to claim 7, characterized by line spacings, smaller compared to modification A, between the pairs of lines at interplanar spacings 3.68 Å and 3.64 Å, 3.51 Å and 3.48 Å and 3.19 Å and 3.15 Å.

9. Modification A according to claim 1 in essentially pure form.

10. Crystal modification A of the compound 1-(2,6-difluorobenzyl)-1H-1,2,3-triazole-4-carboxamide characterized by bands at 3412 cm$^{-1}$ and 3092 cm$^{-1}$ in the FT-IR spectrum.

11. Crystal modification A of the compound 1-(2,6-difluorobenzyl)-1H-1,2,3-triazole-4-carboxamide characterized by bands at 1080 cm$^{-1}$ in the FT-IR spectrum.

12. The crystal modification A' of the compound 1-(2,6-difluorobenzyl)-1H-1,2,3-triazole-4-carboxamide, characterized in that it is identical to the modification A according to claim 2 but has defects in the crystal lattice.

13. The crystal modification A' of the compound 1-(2,6-difluorobenzyl)-1H-1,2,3-triazole-4-carboxamide, characterized in that it is identical to the modification A according to claim 3 but has defects in the crystal lattice.

14. The crystal modification A' of the compound 1-(2,6-difluorobenzyl)-1H-1,2,3-triazole-4-carboxamide, characterized in that it is identical to the modification A according to claim 4 but has defects in the crystal lattice.

15. The crystal modification A' of the compound 1-(2,6-difluorobenzyl)-1H-1,2,3-triazole-4-carboxamide, characterized in that it is identical to the modification A according to claim 5 but has defects in the crystal lattice.

16. The crystal modification A' of the compound 1-(2,6-difluorobenzyl)-1H-1,2,3-triazole-4-carboxamide, characterized in that it is identical to the modification A according to claim 6 but has defects in the crystal lattice.

17. The crystal A' according to claim 7 in essentially pure form.

18. A pharmaceutical composition comprising a pharmaceutically acceptable carrier or diluent and a therapeutically effective amount of crystal modification A of the compound 1-(2,6-difluorobenzyl)-1H-1,2,3-triazole-4-carboxamide according to claim 1.

19. A pharmaceutical composition comprising a pharmaceutically acceptable carrier or diluent and a therapeutically effective amount of crystal modification A' of the compound 1-(2,6-difluorobenzyl)-1H-1,2,3-triazole-4-carboxamide according to claim 7.

20. The crystal modification A' of the compound 1-(2,6-difluorobenzyl)-1H-1,2,3-triazole-4-carboxamide, characterized in that it is identical to the modification A according to claim 10 but has defects in the crystal lattice.

21. The crystal modification A' of the compound 1-(2,6-difluorobenzyl)-1H-1,2,3-triazole-4-carboxamide, characterized in that it is identical to the modification A according to claim 11 but has defects in the crystal lattice.

* * * * *

UNITED STATES PATENT AND TRADEMARK OFFICE
CERTIFICATE OF CORRECTION

PATENT NO.       : 6,740,669 B1
APPLICATION NO.  : 09/125329
DATED            : May 25, 2004
INVENTOR(S)      : Robert Portmann et al.

Page 1 of 1

It is certified that error appears in the above-identified patent and that said Letters Patent is hereby corrected as shown below:

In the Claims

Column 10, line 22 (claim 11) change: "characterized by bands at 1080 cm$^{-1}$ in the FT-IR spectrum."

to

-- characterized by bands at 1080 cm$^{-1}$ in the FT-Raman spectrum. --

Signed and Sealed this
Seventh Day of October, 2014

Michelle K. Lee
*Deputy Director of the United States Patent and Trademark Office*